United States Patent [19]
Bahn et al.

[11] Patent Number: 5,762,502
[45] Date of Patent: Jun. 9, 1998

[54] PROCESS FOR ADHERING COMPOSITES TO HUMAN TEETH

[76] Inventors: Arthur N. Bahn, 916 Audubon Dr., St. Louis, Mo. 63105; Gregory P. Stewart, 5918 Dogwood La., Godfrey, Ill. 62035

[21] Appl. No.: 676,644

[22] Filed: Jul. 11, 1996

[51] Int. Cl.$^6$ ............................................. A61C 5/00
[52] U.S. Cl. ...................... 433/215; 433/228.1; 106/35; 523/116
[58] Field of Search ........................ 433/215, 228.1, 433/9; 106/35; 523/116, 118

[56] References Cited

U.S. PATENT DOCUMENTS

| | | | |
|---|---|---|---|
| 4,593,054 | 6/1986 | Asmussen et al. | 523/118 |
| 4,702,734 | 10/1987 | Terranova et al. | 604/54 |
| 4,735,945 | 4/1988 | Sakamoto et al. | 514/279 |
| 4,776,890 | 10/1988 | Chu | 106/161 |
| 4,789,663 | 12/1988 | Wallace et al. | 514/21 |
| 4,859,186 | 8/1989 | Ranly | 433/228.1 |
| 4,952,613 | 8/1990 | Hosoda | 433/228.1 |
| 4,964,911 | 10/1990 | Ibsen et al. | 106/35 |
| 5,004,501 | 4/1991 | Faccioli et al. | 106/35 |
| 5,023,107 | 6/1991 | Roberts | 427/2 |
| 5,071,958 | 12/1991 | Hammarstrom et al. | 530/344 |
| 5,089,051 | 2/1992 | Eppinger et al. | 106/35 |
| 5,238,491 | 8/1993 | Sugihara et al. | 106/35 |
| 5,256,065 | 10/1993 | Nicholson | 433/228.1 |
| 5,258,067 | 11/1993 | Podszun et al. | 433/228.1 |
| 5,270,351 | 12/1993 | Bowen | 523/116 |
| 5,290,172 | 3/1994 | Sakuma et al. | 433/215 |
| 5,385,728 | 1/1995 | Suh | 424/54 |
| 5,401,783 | 3/1995 | Bowen | 523/116 |
| 5,456,602 | 10/1995 | Sakuma | 433/215 |

OTHER PUBLICATIONS

Van Meerbeek et al., "Comparative SEM and TEM Examination of the Ultrastructure of the Resin–Dentin Interdiffusion Zone," *J Dent Res*, vol. 72, No. 2, pp. 495–501, Feb. 1993.

Aktener, Bekir Oguz, DDS, Ph.D. and Ugur Bilkay, DDS, "Smear Layer Removal with Different Concentrations of EDTA–Ethylenediamine Mixtures," *Journal of Endodontics*, vol. 19, No. 5, pp. 228–231, May 1993, copyright 1993 by The American Association of Endodontists.

Perdigao et al., "In vitro Bonds Strengths and SEM Evaluation of Dentin Bonding Systems to Different Dentin Substrates," *J Dent Res*, vol. 73, No. 1, pp. 44–55, Jan. 1994.

B.H. Sen, et al., "The Smear Layer: A Phenomenon in Root Canal Therapy," *International Endodontic Journal*, vol. 28, pp. 141–148, 1995, copyright Blackwell Science Ltd.

Buonocore, M.G., et al., "A Report on a Resin Composition Capable of Bonding to Human Dentin Surfaces" *Journal of Dental Research*, vol. 35, No. 6, 846–851, Dec. 1956.

DENTSPLY® ProBOND© All–Purpose Bonding Agent phamphlet on instructions for use, 534270 (Jul. 1993), pp. 1–6.

Nakabayashi, N., et al., "Effect of HEMA on bonding to dentin", *Dentin Materials*, Dent Mater 8:125–130, Mar. 1992.

*Primary Examiner*—Nicholas D. Lucchesi
*Attorney, Agent, or Firm*—Kalish & Gilster

[57] ABSTRACT

A process for conditioning dentin surfaces in teeth to provide improved bonding strength between restorative materials and a tooth to be restored is disclosed. The process includes exposing a cut tooth surface to at least one enzyme, and then rinsing the tooth surface with water to remove any residual enzyme, prior to applying the restorative material.

20 Claims, 3 Drawing Sheets

(PRIOR ART)

FIG. 4

(PRIOR ART)

FIG. 5

(PRIOR ART)

5,762,502

1

PROCESS FOR ADHERING COMPOSITES TO HUMAN TEETH

FIELD OF THE INVENTION

The present invention relates, generally, to the field of dental bonding, and more particularly, to an enzymatic process for conditioning dentin surfaces in teeth to provide improved bonding between the restorative materials (composite resins and/or glass ionomer cements, often referred to herein generally as "composites") and the tooth surface being bonded.

When composite resins and glass ionomers are employed alone by conventional means, as restorative filling material, they often fail to bond sufficiently to the tooth surface and leave a gap between the tooth structure and the filling material. When this gap is larger than two microns (two times a millionth of a millimeter), bacteria that adhere to the dental biofilm enter the gap along with nutrients for the bacteria and start the carious process beneath the filling. This process is termed microleakage.

Microleakage is the predominant cause of the reappearance of dental caries beneath dental restorations and the loss of restorative fillings. A strong bonding of the filling materials to both the enamel and the dentin will prevent microleakage and allow the patient to retain the restoration of the tooth. In addition, a strong bond will help prevent fracture of the restoration and tooth by allowing for stress transfer between the tooth and restorative material; i.e., reinforcing each other.

Post-operative sensitivity, due to open dentin tubules, would also be reduced by a better bonding to the dentin. Enzymatic conditioning of the tooth surface to be bonded by the new process described below will significantly improve dentinal bonding and thus avoid the described deleterious effects of a weak tooth bond.

Successful restoration of lost tooth structure in carious teeth requires that the replacement materials be bonded to the remaining tooth structure. Bonding depends on the wetting of the restorative material to the tooth and can provide distinct advantages compared to a non-bonded restoration. These advantages include, but are not limited to: 1.) Elimination of marginal leakage—any gap between the tooth and the restoration leads to marginal leakage of elements that continue the process of dental cavity formation; 2.) Provide resistance to the forces encountered by the tooth during chewing; 3.) Improve retention of restoration of the cavity area; and 4.) Minimize the stress concentrations at the interface of the two materials reducing fracture of the tooth, the bond material, and the tooth/bond interface.

The major cause of failure associated with dental restorative materials are oral bacteria that enter through gaps between the unbonded restorative material and the tooth. Better bonding between these elements would eliminate the problematic gaps.

Newer restorative materials have been introduced, such as the composite dental resins, which promise better bonding to the tooth surfaces. Unfortunately, most of the newer materials do not bond as well as desired to the tooth. This is especially true of the bond to dentin, and leakage at the restorative-dentin interface is still the major cause of failure of these restorations.

THE KNOWN ART

Bonding of a restorative material to the tooth had its first breakthrough with the introduction of acid etching of dental enamel. Enamel, the outer covering of the natural crown of the tooth, is a highly mineralized system. More than 95% of the mass of enamel is inorganic material, most, if not all, of which is in a crystalline state.

In 1955, Buonocore developed the acid etching procedure that conditioned the enamel tooth surface and resulted in strong bonds between the restorative material and the etched enamel. When a 37 to 50% solution of phosphoric acid in water was applied for 60 seconds to the surface of enamel, a pock-marked surface resulted. A polymeric resin, primarily a low viscosity methyl methacrylate was painted over the conditioned enamel surface and cured. High bond strengths, measured by the forces required to pull the surfaces apart, as high as 30 Mega Pascals (MPa) were reported by several investigators.

In subsequent trials, the methylmethacrylate was replaced by composite resin materials consisting of hard, glass-like particles encased in the polymeric resin. The new composites were stronger, shrank less, had lower expansion coefficients, were harder, resisted the forces of wear better, and mimicked the natural color of the tooth. This method of conditioning the enamel with acid has gained universal approval and is today an accepted, commonly used dental procedure.

Even with such new filling materials, while adhesion to the outer covering of the tooth, the enamel was improved, achievement of adhesion to the inner tissue, the dentin, was more difficult. When a dentist drills a cavity preparation, usually, the tooth structure that is removed is mostly dentin. Most of the exposed, cut surfaces are also dentin. In contrast to enamel, dentin is only approximately 65% inorganic crystalline material, and the rest is organic material, consisting largely of collagen fibers. The collagen is a rope-like molecule, insoluble in water and resistant to most enzymes and strong acids. Whenever dentin is drilled, a layer of sludge is formed over the surface of the dentin. This layer has been called the dental "smear layer". The smear layer is a residue of the debris that remains following drilling in cavity preparation and this debris sticks to the cut dentin.

High-speed drilling procedures used in modern dental practices create more of this layer of debris. The smear layer consists of ground-up inorganic calcified matter and organic material which is about 85–95% collagen. The smear layer coating the underlying dentin has a weak bond strength of 1 to 3 MPa which interferes with the bonding of the filling (restorative) material to the tooth.

Since acid etching dentin was accepted in the United States (although still debated regarding its biocompatibility), bonding to dentin has received more attention from researchers. Different acids that etched to varying degrees have been evaluated. Some acids tested removed the smear layer completely, others only partially. But bond strengths were still not appreciably increased.

The problem was largely attributed to the poor wetting of the etched dentin substrate by the polymeric adhesive. The etched dentin substrate, regardless of the acid used, was mostly a demineralized mass of collagen. Depending on the type of acid and the length of etching time (time exposed to the acid), this demineralized collagen was 1–10 microns thick. The hydrophobic, polymeric adhesives would not wet this watery, hydrophilic, low surface energy substrate.

The problem of wetting the etched dentin surface with a hydrophobic adhesive was partially addressed by Nakabayashi when he introduced primers to the adhesive bonding technique. In that procedure, citric acid was used to etch or condition the dentin, producing a demineralized collagen mass, as expected. The demineralized collagen was then treated with a bifunctional primer consisting of hydroxyethylmethacrylate (HEMA) containing a hydrophilic hydroxy group on one end of the molecule and a hydrophobic double carbon bond on the other end of the molecule. When mixed with methylmethacrylate, this solution was able to wet and infiltrate the spaces in the demineralized collagen mass. Scanning electron microscopy analysis of the infiltrated mass have identified an acid resistant layer, 1–5 microns thick, containing these molecules and collagen. This has been termed the "hybrid" layer.

The hybrid layer is believed to create a mechanical bond into the intertubular and peritubular demineralized dentin. Various studies have reported bond strengths to dentin via this hybrid layer of from 5 to 25 MPa. However, our tests indicated a maximum dentin/hybrid layer bond strength, with the above procedure, of only 16 MPa (for comparison, the bond strength to properly etched enamel is 30 MPa).

Almost every dentin bonding agent on the market today claims to bond to dentin via this "hybrid" layer. Many dentin bonding systems use a three step procedure, substantially as described hereafter. First, the enamel and often the dentin are etched. This step is referred to as "conditioning the tooth". It removes the smear layer and demineralizes the outer layer of dentin. The second step involves priming the demineralized dentin. Many primers are not needed on the etched enamel as it is ready for bonding after etching. Primers serve to infiltrate the demineralized dentin and facilitate penetration of the adhesive into the primed layer. Third, the adhesive is placed onto the primed surface. The adhesives are usually cured or polymerized either by visible light at 4800 Angstrom units or by a chemical reaction ("auto cure"). Then, the restorative material is placed in the tooth cavity preparation site.

Common acids used for etching in the above-described, conditioning procedures are phosphoric, citric, malic, and nitric acids. The primers commonly in use include HEMA, PENTA (dipentaerythritol penta acrylate phosphoric acid ester), 4-META (4-methacryloxyethyl trimellitic anhydride), and PMDM (adduct of pyromellitic dianhydride and 2-HEMA). The adhesives used are various forms of methyl methacrylate. There are some systems promoted by dental manufacturers that combine either two or three of the above steps into a one step procedure.

The composite resins and glass ionomers traditionally used for dental bonding do not, by themselves, adhere or bond well to the tooth in a cavity restoration. However, three known methods have been used in attempts to improve the bonding. One of these methods is to acid etch the tooth surfaces with phosphoric or citric acid prior to the bonding procedure. This works well with the enamel surfaces which are primarily composed of inorganic material, but on the deeper dentinal surfaces sufficient bonding to the dentin has not been obtained with only acid conditioning of the tooth.

A second known method provides use of various adhesive substances, such as phosphate esters. Such esters have been added and do improve the bonding on the enamel surfaces that have been previously acid etched, but fail to improve bonding to the dentin.

A third method to improve bonding has been to add adhesion-promoting agents e.g. primers such as PENTA, acetone and ethanol. These surface-active comonomers prepare a more "wettable" dentin surface and do somewhat improve bonding, either chemical or mechanical, to dentin. However, bonding obtained by this method is still significantly less strong than the bond to etched enamel. This lower strength bond to dentin is largely due to the effect of the acid on the dentin.

When bonding enamel, there is little difference encountered between untreated enamel and etched enamel. Both are primarily inorganic calcium phosphate. But etched dentin is highly different from unetched dentin. The smear layer or "sludge" generated on the surface of the dentin by drilling of the tooth interferes with the bonding process and must be altered or removed to allow for optimally strong bonding.

Acid removal or alteration of the smear layer formed on drilled dentin presents problems. Acid etching removes the inorganic calcium phosphates but only denatures the organic phase of dentin, such organic phase being primarily collagen. If the dentin smear layer is not removed by acid etching, the remaining debris, (primarily collagen), inhibits penetration of the adhesive. This inhibits both mechanical and chemical bonding to the inorganic phase of dentin.

The described inhibition is particularly seen because much of the remaining collagen from the smear layer has been denatured by the heat of the drilling, and accordingly is not entirely dissolved by the acid, nor wetted by the detergents. Also, because the acid dissolves primarily the inorganic phase of dentin, it is possible to excessively etch the smear layer. So, bonding by this latter process may result in removal of the smear layer, but at the expense of overetching, beneath the smear layer and creating a collagen mass which covers the underlying dentin; in effect creating a new smear layer. This newly created smear layer is effectively layers of collagen which cover the dentin and prohibit wetting and intermixing of the adhesive with the stronger, more mineralized dentin underlying the conditioned surface.

Accordingly, a need exists in the dental industry for a dental bonding method which provides a stronger bond than presently achieved by conventional methods, especially when dentinal bonding is required, and which method is safe for both the patient and clinician and which is further amenable to use in a clinical setting with minimal training by individuals already skilled in dental bonding procedures.

It is further among the goals of the present invention, having the features indicated, that the new dental bonding method be available at a cost which is less than that associated with alternative dental procedures, such as replacement of a tooth or forming an artificial crown thereon, and which procedure does not require a significant increase in or requires no more time and inconvenience than such alternative procedures or other known methods of bonding.

SUMMARY OF THE INVENTION

This invention relates to improving the bonding of dental restorative material to the dentin of a tooth being treated by enzymatically (1) removing the collagen of the smear layer, or (2) by removing the natural collagen-rich surface layer that is produced by "over-etching" the dentin. A stronger, more mineralized, more wettable surface is obtained and the fluid composite resins and other restorative material can flow into the channels vacated by the enzymatically removed collagen. As a result of the new process, described below, when these resins set and become solid, multiple fingers of resin extend into the dentin creating a strong mechanical or chemical bond.

In the new process the standard method of conditioning with acid is improved or replaced by the unique step of exposing the dentin of the cavity preparation to various proteolytic enzymes. Optional acid etching of the dentin may be added to promote even greater adhesion by combining acid etching with the new enzyme treatment of the dentin.

The dentin portion of a tooth, beneath the enamel layer, consists of both inorganic calcium phosphate and organic protein, principally collagen. The heat generated during the dental drilling process denatures the collagen and mixes it with the inorganic material. The resulting sludge of denatured collagen and calcified element has been called the "smear layer". It is this layer that coats the remaining dentin and hinders bonding between such remaining dentin and the composite material to be bonded thereto.

Our tests have shown that much of the smear layer can be removed by exposure to proteolytic enzymes, thus permitting improved bonding. The new method described hereafter, includes treating the tooth surface with enzymatic conditioning to remove much of the organic smear layer and thus prepares a wettable surface that will bond surprisingly strongly to dental restorative materials.

Accordingly, in furtherance of the above objects, the present invention is, briefly, an improved method for achieving dental bonding. The process for conditioning dentin surfaces in teeth provides improved bonding strength between restorative materials and a tooth to be restored. The process includes exposing a cut tooth surface to at least one enzyme, and then rinsing the tooth surface with tap water to remove any residual enzyme, prior to applying the restorative material in an otherwise conventional manner.

The invention is further, briefly, the use of a mixture of collagenase/dispase enzymes in the above process.

These and other advantages of the invention will be in part apparent and in part pointed out hereinbelow.

DESCRIPTION OF PRACTICAL EMBODIMENTS

Generally speaking, the new bonding method is accomplished by treating the smear layer with enzymes, preferably metalloprotein enzymes (collagenases) and neutral proteases to remove the residual organic material. The use of such enzymes for conditioning dentin is a new use for these products. This optionally may be preceded by a brief etching of the smear layer with acid, in known manner. Throughout the specification and claims the relevant tooth surface is sometimes referred to as a "cut" tooth surface. For purposes of this document, this term will mean a tooth surface that has been cut, drilled, sanded, or otherwise interrupted to such an extent that the dentin layer is revealed.

The organic material to be removed enzymatically is denatured collagen. Collagen 1 is the predominant protein in tooth dentin and through the process of drilling the tooth, especially with high-speed handpieces, it becomes denatured. Extreme heat denatures the protein, causing unravelling of the braided rope-like structure of the collagen molecule.

Broad activity metalloproteinases, such as a mixture of collagenases, digest most of the denatured surface proteins in the smear layer, as well as some of the normal collagen molecules. The residual surface protein that the collagenases cannot digest is hydrolyzed by the addition of neutral proteases.

In this manner, the organic surface layer of the dentin is preferably removed, resulting in an altered dentin surface which is more amenable to wetting by a hydrophobic adhesive. After enzymatic treatment, the resulting surface has a higher ratio of inorganic to organic matter. This benefits wetting as it raises the surface energy of the newly treated surface, as compared to the non-treated surface.

Higher energy surfaces are more readily wetted by the primers and/or adhesives commonly used in dentistry. In addition, the enzymatically treated surface is stronger, thus affording stronger bonding to the adhesive. The subsurface collagen remains intact. This allows the resin to flow into the conditioned dentin surface and, when polymerized, to form stable "fingers" into the body of the dentin. These extensions or fingers anchor the resins and create a stronger bond.

This concept was tested in a series of in vitro experiments. Human teeth were collected from an oral surgery clinic following extractions. Transverse cuts resulted in the dentin discs covered with smear layer. These discs were tested against a variety of a collagenases by immersing the discs in various concentrations of the enzyme mixtures and varying the time of exposure. SEM Analvsis:

The removal of the smear layer was tested by examining the discs by scanning electron microscopy ("SEM"). Examples of the results of these tests are shown in FIGS. 1–5. The SEM tests revealed that, as compared to controls, the enzymes removed the smear layer sufficiently so that the open dentinal tubules can be visualized (See FIGS. 1 and 2). As explained, these tubules critically assist in development of the improved bonding between the restorative material and the dentin, and thus can be expected to be a major advancement in overcoming the problem of microleakage which has plagued the use of composite materials in dentistry. The SEM micrographs show conclusively that the etching achieved by the new method is successful.

Figure 5:
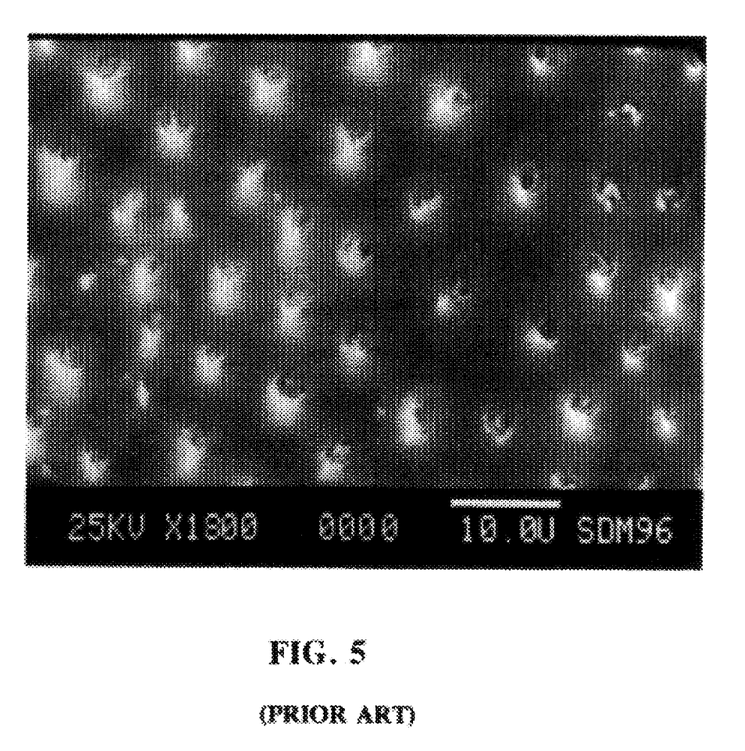
FIG. 5 is an SEM of a sample of dentin conditioned by a conventional method with a 10% polyacrylic acid solution for 20 seconds, followed by a 20 second tap water rinse.

The collagenase treated discs (FIGS. 1 and 2) were compared to positive controls of phosphoric acid etched dentin (FIG. 3) (a known method), as well as those treated with ethylenediamineteracetic acid (EDTA) (FIG. 4), a known chelating agent that calcifies inorganic calcium salts such as the hydroxyapatite found in teeth, and also those conditioned with 20% polyacrylic acids (FIG. 5).

Figure 1:
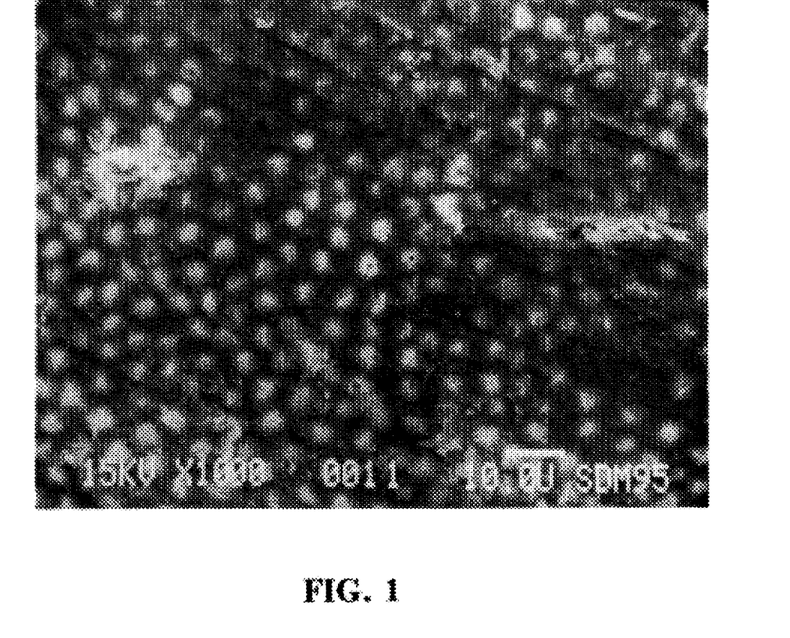
FIG. 1 is a scanning electron micrograph (SEM) of a sample of dentin conditioned according to the method of the invention, with enzyme solution at 1 mg/ml, for two (2) minutes, followed by tap water rinse.
Figure 2:
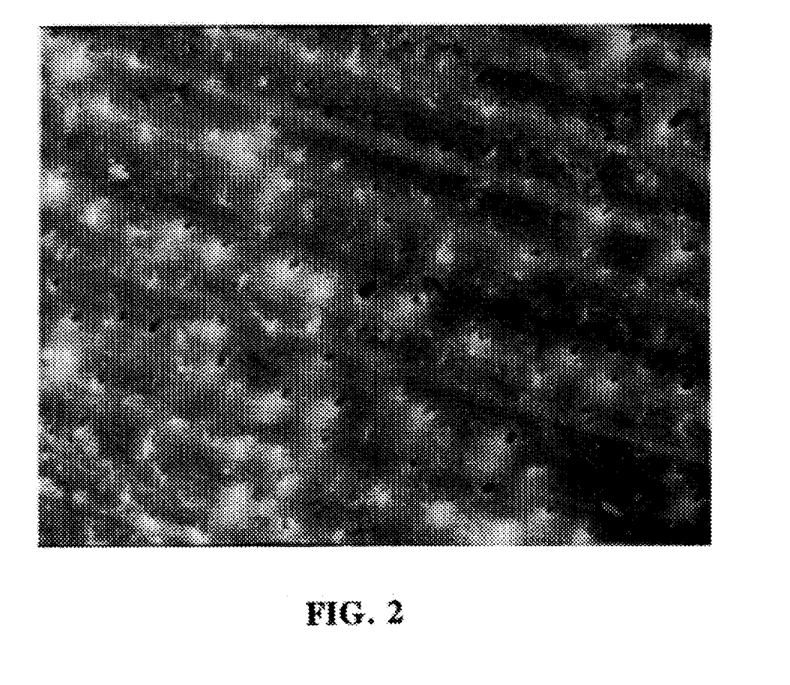
FIG. 2 is an SEM of a sample of dentin conditioned according to the method of the invention with enzyme solution at 1/16 of 1 mg/ml for two minutes, followed by a tap water rinse for 20 seconds.
Figure 3:
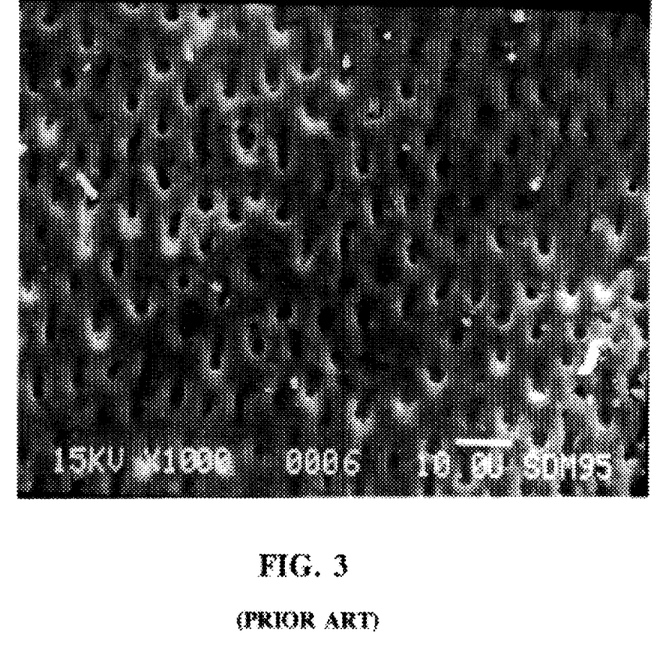
FIG. 3 is an SEM of a sample of dentin conditioned by a conventional procedure with 37% aqueous solution of phosphoric acid for 30 seconds, rinsed with tap water for 20 seconds.
Figure 4:
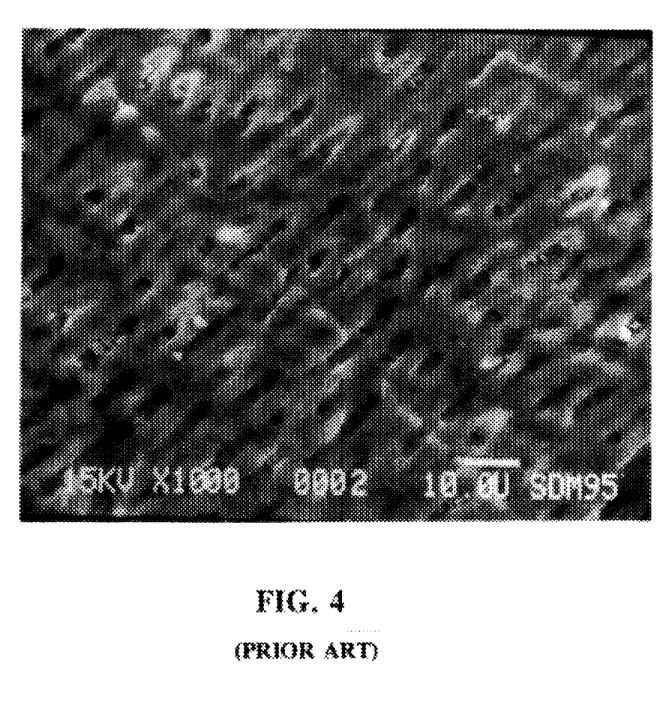
FIG. 4 is an SEM of a control sample of dentin conditioned with 17% EDTA for one (1) minute followed by a 20 second tap water rinse.

The results of one of the above-described tests revealed that a commercial mixture, generally referred to as collagenase/dispase (presently available from Sigma Chemical Co. Cat. No. C0299), at a concentration of 1 mg/ml for two minutes (FIG. 1), removed the smear layer to the same degree as the EDTA (FIG. 4), and substantially as well as did the phosphoric acid etching tested (FIG. 3).

To further explain the SEM micrographs of the figures, dentin consists of a tubular structure running from the pulp outwardly to the side of the tooth, which is usually covered with enamel. Essentially, hollow tubes filled with fluid run from the pulp outward. The diameter and density of these tubules changes as they radiate from the pulp. Thus, when looking as SEM micrographs of etched dentin, the size and density of the openings seen is a function of where on the tooth the sample was taken, not of the degree of etch obtained. Rather, anytime openings are seen, a satisfactory etch is indicated.

In making the samples for the above SEM analysis, a disc of dentin was cut from the extracted tooth. Such cutting produces a smear layer covering the dentin like a smooth blanket and fills in the cut ends of the tubules. Then, the cut surface of the disc was etched, or "conditioned".

By such SEM testing it can be determined whether or not the outer (blanket) smear layer and smear plugs inside the end of the tubules have been removed. The usual previous way of doing this was with a strong acid. Other substances, such as alcohol and hydrogen peroxide, etc. will not remove the smear. Although it cannot be determined by viewing the micrographs whether the inter tubular (between tubes) dentin is mostly organic or inorganic, it is known that when using an acid to etch, the acid removes primarily mineral, i.e., inorganic portions of dentin, leaving organic-rich dentin behind. Such organic-rich dentin is a low energy surface which is very hard to wet, and forms a very weak bond with composite dental materials. Because the enzymes used in the new process remove primarily organic dentin, the opposite of acids, the etched surface produced by the present process is more inorganic, higher in energy and stronger, than one etched by conventional acid methods.

The results of the above SEM micrographic testing, without any details of the experimental methods, were presented at the 24th meeting of the American Association of Dental Research on Mar. 9, 1995, and an abstract of that presentation was published in *The Journal of Dental Research*, Volume 74 (Special Issue), page 33, abstract #170. Bonding kits available from manufacturers had not been tested at that time, as bonding strengths of teeth enzymatically conditioned had not been fully mechanically tested.

Because proteolytic enzymes, by definition, destroy proteins, it has not been previously considered possible to use such enzymes for dental bonding, due to the problematic damage to surrounding tissues and associated discomfort to the patient. It has been determined, however, that when used carefully, properly diluted and applied, such enzymes have a surprising and beneficial effect on the strength of dentinal/ restorative bonding in comparison to previously known methods of restorative tooth bonding.

The proteolytic enzymes employed for the first time for dental bonding in the present method are mixtures of metalloproteinases (collagenases) and neutral proteases. Although, not all possible mixtures of such enzymes been tested as yet, it is expected that the results disclosed herein of tests so far performed on dentin conditioned by the new method will exemplify the results from future tests with other reasonable mixtures.

Our results show that conditioning with these enzymes (metalloproteinases and neutral proteases) according to the invention improves the adhesion of the composite filling material to the cut tooth surface. Conditioning with the enzymes after acid etching even further improves the adhesion of composite resins and glass ionomers to dentin.

Other metalloenzymes (metalloproteinases) used in the new method are mixtures of known collagenases of bacterial origin and crustacean origin, together with neutral proteases. Specifically, the collagenases are obtained by conventional methods from *Clostridium histolyticum*, Types F, H, L and N, such as, for example, which are commercially available from Sigma Chemical Co. (Sigma Blend Collagenases, and specifically clostridiopeptidase A; EC 3.4.24.3) *Achromobacter iophagus* (Collagenase, EC 3.4.24.8), Collagenase/ Dispase (EC 3.24.8/EC 3.4.24.4) from *Achromobacter iophagus/Bacillus polymyxa*, and Collagenolytic proteinase from the Kamchatka crab, *Paralithoides camtshatica* hepatopancreas.

The neutral proteinase is preferably obtained in known manner from *Bacillus Dolymvxa*. Various mixtures of the enzymes diluted in physiological saline have been tested at various concentrations ranging from 1 mg/ml to 0.625 mg/ml. Our results show that diluting the enzyme concentration to one-sixteenth ($1/16$) of the normal 1 mg/ml concentration did not affect its ability to remove the smear layer and properly condition the dentin, as shown in the sample in FIG. 3. Alteration of exposure time from 1 to 20 minutes produced the same degree of conditioning. Using a shorter exposure time and the diluted enzyme concentration will protect the patient from any possible adverse effects of exposure to the enzymes. Thus, it is preferred that an enzyme exposure time of about one minute be used, clinically. However, exposure in the range of about one minute to about 20 minutes are considered sufficient, and other times slightly less, and certainly longer, are also considered to be within the scope of the invention.

A second series of experiments was performed using only the metalloprotein Collagenase/Dispase ("CD") enzyme to condition the discs and composite resin was then added. The bond shear strength of this resin-dentin interface was measured on an Instron Universal Testing machine in the usual manner. It was found that bond strengths equivalent to conditioning only with phosphoric acid were obtained.

A third series of experiments was performed in which the dentin discs were first etched with phosphoric or polyacrylic acids for one minute, washed with tap water and then treated with the CD enzyme at various concentrations, and for various lengths of time. Other reasonable lengths of acid etching time are considered within the scope of the invention. Conventional tests for shear bond strength using several commercially available bonding materials revealed an increase in bond strength of between a 7 to 140 percent bonding of the composite resins to the dentin, as compared to acid etching only.

Other collagenases are also considered to be suitable for the new procedure and are being tested in order to determine which combination of enzymes and acid etching will condition the dentin surface so that the conditioning product will be most effective, safest and the most economical system for use on human patients.

Other metalloprotein enzymes for improved bonding of glass ionomer restorative materials are also considered suitable for use in the new dental bonding procedure.

The most effective mixture tested, to date, by in vitro testing of slices (or "discs") of extracted teeth is a mixture of the *A. iophagus* collagenase and the neutral protease from *B. polymyxa* at a concentration of 1 mg/ml for one minute at room temperature.

Enzymatic conditioning of the dentin can replace acid etching of the tooth or augment acid etching, depending on the specific adhesive system being used. Although the acids used in etching are known not to be highly biocompatible, as they can cause irritation to exposed tissues, they are so diluted during the rinsing procedure, that their harmful effects are neutralized.

This dilution effect also applies to the enzyme solution used herein, which otherwise may cause untoward effects on the sensitive mouth tissues. Not only does rinsing dilute and reduce the exposure of the patient to the enzyme, but as mentioned earlier, it can be diluted 16:1 and still effectively condition the dentin to the same degree. In fact, it is known that even hydrofluoric acid, a highly caustic acid, is used intra-orally for etching porcelain restorations during repair procedures and presents no biocompatibility problem, as long as rinsing and suction are performed in a normal, clinical manner.

Bond Strength Tests:

As a specific example of the new procedure, bond strengths have been tested by bonding composite resins, and other components of commercially available dentin bonding kits, to dentin samples with and without enzymatic conditioning. Dentin bonding kits suitable for this purpose include, for example, those sold under the tradenames OPTIBOND by Kerr Corporation, SCOTCHBOND MULTI-PURPOSE PLUS, by 3M Corporation, and FUJI II LC by GC Corporation.

First, freshly extracted teeth are sanded to expose dentin surfaces. The sanded teeth are then mounted in 18 mm diameter holes of a 6 mm thick Teflon plate using "auto cure" acrylic resin. Dentin surfaces are sanded flat with the Teflon plate using 320 grit silicone carbide grinding paper on a polishing wheel.

In the test method mounted teeth are always kept wet and stored at 37° C. when not being used. The dentin surface to be bonded is conditioned as specified, appropriate primers and adhesives applied, following manufacturers directions explicitly (concerning rinsing, drying, light curing), and a 0.001 inch thick polyethylene sheet with a 5 mm diameter hole is then centered over the prepared dentin.

A matching Teflon plate with a 7 mm diameter hole is then centered over the 5 mm diameter hole in the polyethylene sheet. Restorative material, either composite or glass ionomer, is then condensed into the 7 mm, tapered, diameter hole to a depth of 2 mm. Light curing is done as per manufacturer's directions. Samples are stored for 48 hours in 37° C. water bath and tested for shear strength, as measured on a known mechanical test device, commercially available, for example, from Instron, operated at a cross head speed of 2 mm/minute. Samples are held in the Instron test device by a wire looped through a hole in one of the Teflon plates, and a rod placed through a hole in the other Teflon plate and secured to the Instron test cell.

Bond Strenath Results:

Test results of the above described tests varied somewhat among samples, but overall there was a decided improvement in bond strength of the enzymatically treated dentin discs over the controls only etched with acid. Other discs were first acid etched, washed, and then treated with the enzyme mixture. The results with these disc tests also varied with the sample, but overall, as shown in the chart below, there was found a significant further increase in bond strength as compared to the dentin discs which were only acid etched, as well as to the discs which were only enzymatically treated.

Specific Examples of Shear Bond Strength:

| Sample | Shear Bond Strength |
|---|---|
| Optibond (etch with 37% phosphoric acid | 14.5 Mpa |
| Optibond (etch with CD enzyme only | 10.6 Mpa |
| Optibond (etch with 37% phosphoric acid + CD enzyme | 16.5 Mpa |

-continued

Specific Examples of Shear Bond Strength:

| Sample | Shear Bond Strength |
|---|---|
| Scotchbond Multi-Purpose (37% phosphoric acid only | 4.5 MPa |
| Scotchbond Multi-Purpose (CD enzyme only) | 6.2 MPa |
| Scotchbond Multi-Purpose (37% phosphoric acid & CD enzyme) | 7.1 MPa |
| Fuji II L C (etch with 10% phosphoric acid) | 3.5 MPa |
| Fuji II L C (etch with enzyme only) | 5.3 MPa |
| Fuji II L C (10% polyacrylic acid + enzyme) | 8.5 MPa |

Accordingly, our tests have revealed that use of enzymes, as described above, with or without acid, causes etching of the smear layer to such an extent as to provide an exposed tooth surface with surprisingly strong bond strengths when bonded to commercial dental restorative materials.

In view of the foregoing, it will be seen that the several objects of the invention are achieved and other advantages are obtained.

Although the foregoing includes a description of the best mode contemplated for carrying out the invention, various modifications are contemplated.

As various modifications could be made in the methods herein described without departing from the scope of the invention, it is intended that all matter contained in the foregoing description shall be interpreted as illustrative rather than limiting.

What is claimed is:

1. A process for conditioning dentin surfaces in teeth to provide improved bonding strength between restorative materials and a tooth to be restored comprises:
   exposing a cut tooth surface to at least one enzyme, and then rinsing the tooth surface to remove any residual enzyme, prior to applying the restorative material,
   to thereby etch the smear layer created during cutting of the tooth and thus provide a cut tooth surface having improved bonding strength when bonded to restorative materials.

2. The process of claim 1, wherein the step of exposing the tooth surface to at least one enzyme is performed using at lease one metalloproteinase.

3. The process of claim 2, wherein the step of exposing the tooth surface to at least one metalloproteinase is performed using at least one collagenase.

4. The process of claim 3, wherein the step of exposing the tooth surface to at least one collagenase is performed using a collagenase from *Achromobacter iophasus*.

5. The process of claim 3, wherein the step of exposing the tooth surface to at least one collagenase is performed using a mixture of collagenases from *Clostridium histolyticum*.

6. The process of claim 1, wherein the step of exposing cut tooth surface to at least one enzyme is performed using a mixture of collagenase/dispase enzymes.

7. The process of claim 6, wherein the step of exposing the cut tooth surface to a mixture of collagenase/dispase enzymes is performed using a mixture of collagenase/dispase from *Achromobacter iophasus/Bacillus polymyxa*.

8. The process of claim 6, wherein the step of exposing the tooth surface to a mixture of collagenase/dispase is performed using a collagenase/dispase concentration of from about 0.625 mg/ml to about 1 mg/ml.

9. The process of claim 6, wherein the step of exposing the cut tooth surface to a mixture of collagenase/dispase is performed using a concentration of 1/16th of 1 mg/ml.

10. The process of claim 1, wherein the step of exposing the tooth surface to at least one enzyme is performed using a collagenolytic proteinase.

11. The process of claim 10, wherein the step of exposing the cut tooth surface to a collagenolytic proteinase is performed using a collagenolytic proteinase *Paralithodes camtshatica* hepatopancreas.

12. The process of claim 1, wherein the step of exposing the cut tooth surface to at least one enzyme is performed using a neutral protease.

13. The process of claim 1, wherein the step of exposing the cut tooth surface to at least one enzyme is performed for a period of time in the range of approximately one minute to approximately 20 minutes.

14. The process of claim 1, wherein the step of exposing the cut tooth surface to at least one enzyme is preceded by exposing the cut tooth surface to an acid.

15. The process of claim 14, wherein the step of exposing the cut tooth surface to an acid is performed for approximately one minute.

16. The process of claim 14, wherein the step of exposing the cut tooth surface to an acid is performed using phosphoric acid.

17. The process of claim 16, wherein the phosphoric acid is used at a concentration of approximately 37%, aqueous.

18. The process of claim 14, wherein the step of exposing the cut tooth surface to an acid is performed using polyacrylic acid.

19. The process of claim 1, wherein the step of rinsing is performed with water.

20. The process of claim 19, wherein the step of rinsing is performed for approximately twenty seconds.

* * * * *

UNITED STATES PATENT AND TRADEMARK OFFICE
CERTIFICATE OF CORRECTION

PATENT NO. : 5,762,502
DATED : June 9, 1998
INVENTOR(S) : Bahn, Arthur N. et al.

It is certified that error appears in the above-indentified patent and that said Letters Patent is hereby corrected as shown below:

Claim 11, Column 11, line 6, after "proteinase" insert --from--.

Signed and Sealed this

Seventeenth Day of November, 1998

Attest:

BRUCE LEHMAN

*Attesting Officer*     *Commissioner of Patents and Trademarks*